(12) United States Patent
Sandal et al.

(10) Patent No.: US 7,129,394 B2
(45) Date of Patent: Oct. 31, 2006

(54) TRANSGENIC TEA THROUGH BIOLISTIC USING LEAF EXPLANTS

(75) Inventors: Indra Sandal, Himachal Pradesh (IN); Amita Bhattacharya, Himachal Pradesh (IN); Paramvir Singh Ahuja, Himachal Pradesh (IN)

(73) Assignee: Council of Scientific and Industrial, New Delhi (IN)

( * ) Notice: Subject to any disclaimer, the term of this patent is extended or adjusted under 35 U.S.C. 154(b) by 251 days.

(21) Appl. No.: 10/051,383

(22) Filed: Jan. 22, 2002

(65) Prior Publication Data

US 2004/0216191 A1    Oct. 28, 2004

(51) Int. Cl.
*A01H 4/00*    (2006.01)
*A01H 5/00*    (2006.01)
*C12N 5/04*    (2006.01)
*C12N 15/09*    (2006.01)
*C12N 15/82*    (2006.01)

(52) U.S. Cl. .................. 800/293; 800/278; 800/288; 435/419; 435/430; 435/430.1; 435/431; 435/470

(58) Field of Classification Search ................ 800/278, 800/298, 293, 288; 536/23.1; 435/419, 435/430, 430.1, 431, 470
See application file for complete search history.

(56) References Cited

OTHER PUBLICATIONS (Hansen et al., 1999, Trends in plant Science, vol. 4, pp. 226-231, see page 230).*
Potrykus, Gene Transfer to Cereals: An Assessment, 1990, Biotechnology, 8(6): 535-542 p. 538, column 2, 3rd full ).*

* cited by examiner

*Primary Examiner*—David T. Fox
*Assistant Examiner*—Georgia Helmer
(74) *Attorney, Agent, or Firm*—Foley & Lardner LLP; Richard C. Peet

(57) ABSTRACT

The present invention relates to Production of transgenic tea (*Camellia sinensis* (L.) O. Kuntze) through biolistic.

Figure 1:
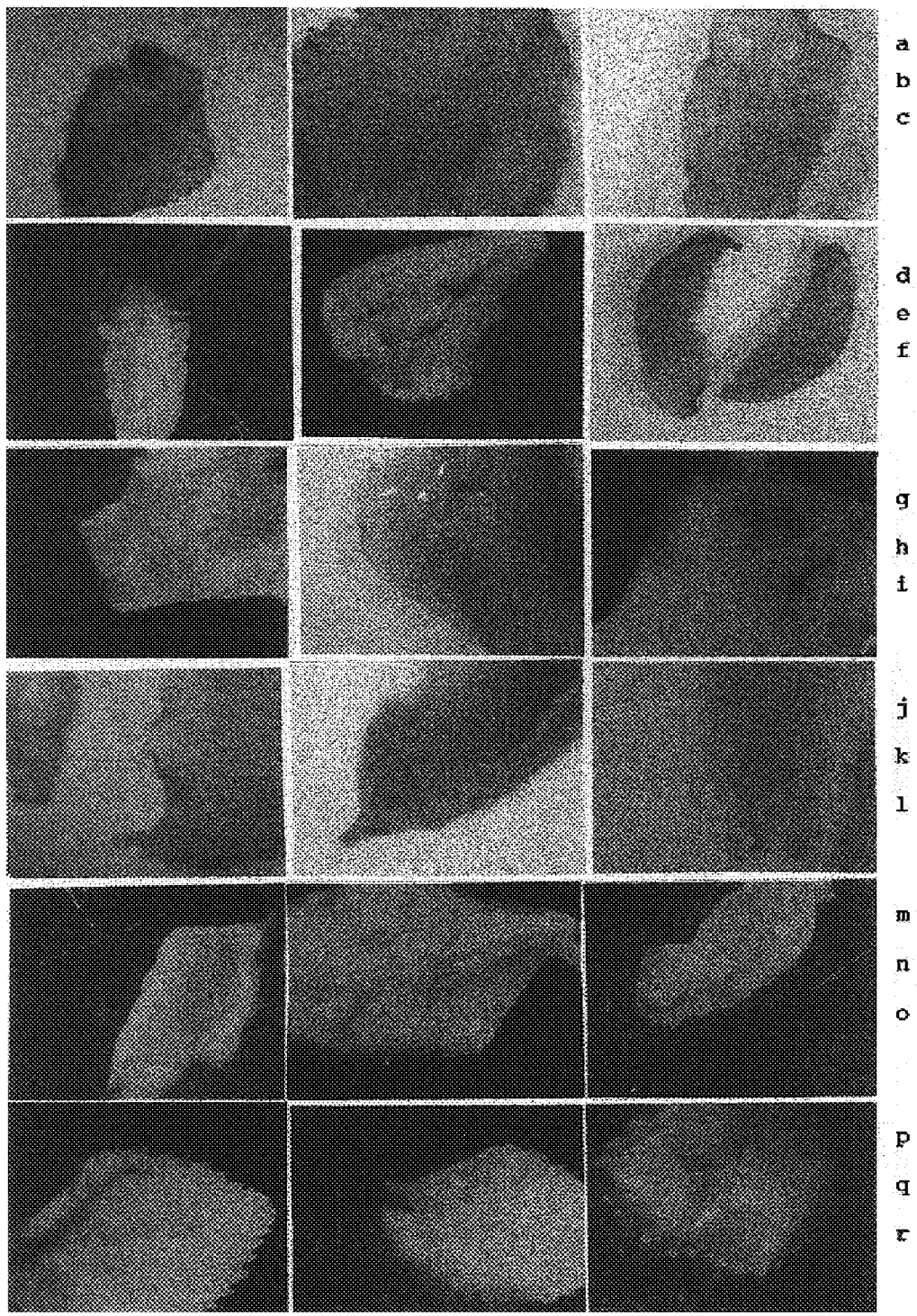

29 Claims, 1 Drawing Sheet
(1 of 1 Drawing Sheet(s) Filed in Color)

TRANSGENIC TEA THROUGH BIOLISTIC USING LEAF EXPLANTS

FIELD OF THE INVENTION

The present invention relates to Production of transgenic tea (*Camellia sinensis* (L.) O. Kuntze) through biolistic

BACKGROUND OF THE INVENTION

Tea is a popular caffeine containing beverage with anti-cancerous properties (Jankun, J., Selman, S. H., Swiercz, R. Why drinking green tea could prevent cancer. Nature 5:561; 1997). Tea is also an important employment generator and a major foreign exchange earner in all the tea growing areas of the world (Wilson, K. C. Botany and Plant Improvement In: Wilson R. C., ed. Coffea, Cocoa and Tea. CABI Publishing, Wallingford, UK: 167–173; 1999). While, the total production of tea is not sufficient enough to meet the demands of the domestic and the world markets (Kabra, G. D. Tea statistics for 1999 In: Tea time, Vol. VIII, No. 3 September–November 1999, 30–31; 1999). The yield and quality of tea is further reduced by different biotic (fungi, pests and viruses) and abiotic (frost, hail, chilling, drought, nutritional deficiencies etc.) stresses (Wilson, K. C. Botany and Plant Improvement In: Wilson R. C., ed. Coffea, Cocoa and Tea. CABI Publishing, Wallingford, UK: 167–173; 1999). Although for most crops, higher yield per unit area is of primary importance but the major objective for tea is improved yield coupled with better adaptibility and cup characters. Moreover, the world market has critical standards for tea from different parts of the world to which the products must conform in order to attain high commercial value.

Superior stress resistant tea plants combining both yield and cup quality are therefore, of utmost importance (Barua, D. N. The tea plant of commerce In: Barua, D. N., ed. Science and practice in tea culture, Tea Research Association Calcutta; 53–68; 1989). Crop improvement programmes also aim at reasonable degree of morphological homogeneity in the progeny. Long life cycles of almost 10 years coupled with high degree of self incompatibility and inbreeding depression (Barua, D. N. The tea plant of commerce In: Barua, D. N., ed. Science and practice in tea culture, Tea Research Association Calcutta; 53–68; 1989) are the major limitations for conventional tea breeding programmes. The important and efficient alternative for overcoming these limitations is genetic transformation through *Agrobacterium tumefaciens* or biolistic wherein desired genes can be directly introduced into the plant genome.

Biolistic has been successfully employed in the genetic improvement of woody perennials specially when the plants have long life cycle or when the basic information about plant inheritance is lacking. Thus genetic transformation through biolistic holds a tremendous potential in tea specially when the leaves are used as the initial explants. More so, because leaf explants despite having a tremendous potential for crop improvement are highly recalcitrant to *Agrobacterium tumefaciens*-mediated transformation probably due to the presence of certain phenolics (Biao Xi, Toru K, Jian Xu, Yongyan B Effect of polyphenol compounds in tea transformations. Abstr. no. 314. In: American Society of Plant Physiologists, Plant Biology 1998).

Although some tea clones have been identified which are high yielding as well as of high quality, yet these are susceptible to blister blight disease. Biotechnological improvement through homogenous tissues like leaf explants is required in these clones because heterogeneous tissues like cotyledon explants would result in genetic variability and loss of the desirable character of high yield and good quality. Therefore, use of leaf explants was important. However, the transformation of leaves through *Agrobacterium tumefaciens* is known to be in effective due to high content of certain polyphenols.

It was realized that primarily three factors viz. (i) increased surface area for maximum particle penetration, (ii) minimum cell damage/injury and (iii) maximum regeneration efficiency were required in order to make the transgenic protocol successful. Therefore, a method for biolistic mediated transgenic production of tea (*Camellia sinensis* (L.) O. Kuntze) using leaf explants was developed taking into account the above three factors in order to enable further genetic improvement of selected elites.

Genetic transformation through *Agrobacterium tumefaciens* was first initiated in tea leaves (Matsumoto S and Fukai M 1998 *Agrobacterium tumefaciens* mediated gene transfer in tea plant (*Camellia sinensis*) cells. Japan Agricultural Research Quarterly, 32: 287–291; Matsumoto S and Fukai M 1999 Effect of acetosyringone application on *Agrobacterium* mediated gene transfer in tea plant (*Camellia sinensis*), Bulletin of the National Research Institute of vegetables, ornamental plants and tea, Shizuoka, Japan, 14: 9–15) wherein transformed leaf callus was produced using 500 µM Acetosyringone was selected at 200 µg/ml kanamycin. These transformed calli showed PCR amplification for nptII gene primers. The major draw back is that transgenic plants could not be regenerated from these transformed leaf calli. Even induction of callus on the leaves required a very high dose of the costly chemical Acetosyringone.

Genetic transformation through *Agrobacterium tumefaciens* has also been attempted by Biao (Biao Xi, Toru K, Jian Xu, Yongyan B Effect of polyphenol compounds in tea transformations. Abstr. no. 314. In: American Society of Plant Physiologists, Plant Biology 1998) wherein leaf and cotyledons were tested. The draw back of the report is that the leaf explants could not be significantly infected with *Agrobacterium tumefaciens* and could not be transformed because of high content of phenolics mainly catechins.

OBJECTS OF THE INVENTION

The main object of the present invention is to provide a method for production of transgenic tea (*Camellia sinensis* (L.) O. Kuntze) through biolistic using leaf explants which obviates the drawbacks as detailed above. The novelty of this method is that it is the first successful method of transforming leaf explants of tea in high frequency with the use of biolistics so as to produce transgenic plants.

Another object of the present invention is the achievement of a combination of increased surface area for maximum particle penetration, minimum cell damage/injury and maximum regeneration efficiency.

Another object of the present invention is to develop different combinations (354) of the parameters that affect biolistic in order to achieve (i) increased surface area for maximum particle penetration, (ii) minimum cell damage/injury and (iii) maximum regeneration efficiency.

Another object of the present invention is to overcome some of the problems faced in certain steps during biolistics.

Another object of the present invention is the production of transgenic tea resistant to biotic and abiotic stresses.

Yet another object of the present invention is to produce tea plants with higher yield and good cup quality.

Yet another object of the present invention is to genetically transform elite tea plants so as to improve both quality and yield.

Yet another object of the present invention is to produce de-caffeinated tea plants.

Yet another object of the present invention is to produce transgenic tea plants with sweet tea leaves using genes like thaumatin and lectins etc.

DETAILED DESCRIPTION OF THE INVENTION

The invention relates to production of transgenic tea (*Camellia sinensis* (L.) O. Kuntze) through novel combination of 360 parameters for the production of transgenic tea (*Camellia sinensis* (L.) O. Kuntze) through biolistic. The method of the invention comprises (a) prior to the subjection of the leaf explants to 360 combinations, treatment of leaf explants with different concentrations (0.25–0.75M) of different osmotic agents ranging from sucrose, myoinositol, sorbitol, mannitol alone, combinations of mannitol and sorbitol and liquid basal MS medium (Murashige T. and Skoog F. A revised medium for rapid growth and bioassays with tobacco tissue cultures. Physiol. Plant. 15: 473–497; 1962) supplemented with vitamins like thiamine-HCl (0.1 mg/l), pyridoxine-HCl (0.5 mg/l) and nicotinic acid (0.5 mg/l) together with glycine (2.0 mg/l) for different time periods ranging from 2 to 8 hrs (b) drawing of concentric circles of variable diameter ranging from 2.0–9.0 cm, on a transparent polythene sheet wherein the diameter of the outermost circle is same as that of a 9.0 cm petridish (c) arrangement of leaf explants with the adaxial surface up on the regeneration medium for bombardment (d) arrangement of leaf explants on the regeneration medium within the different concentric circles (2.0 to 5.0 cm) of 9.0 cm Petri-dishes for maximum spread of pRT99GUS plasmid DNA coated micro-projectiles produced by BioRad (e) sterilization of the gold particles by washing with 70% alcohol followed by sterile water for three times each (f) suspension of 60 µg of gold particles in 0.5–1.5 ml sterile distilled water (g) dispension of 25–60 µl of this suspension in 1.5 ml Eppendorf tubes for each bombardment (h) mixing of 50 µl of gold suspension with 10 µl of different concentrations of pRT99GUS plasmid DNA (0.5–5 µg/µl), 40–50 µl of 1.5–3.5M $CaCl_2$ and 10–50 µl of 0.5–2.0M spermidine free of phosphate salts with simultaneous vortexing from time to time, spinning for 5–20 seconds at 500–1100 rpm followed by removal of the supernatant and washing with 70% ethanol and final suspension in 50–100 µl of 100% ethanol (i) coating of 10 µl suspension of gold particles and DNA on sterile macro-carriers (BioRad) with immediate vortexing (j) development of 360 combinations comprising of: gap distances or distance between the rupture disc and the macro-carrier (¼–⅜ inches alone and in combination), macrocarrier flight distance or the distance between macrocarrier and stopping screen (6–16 mm), and target distance or distance between the microprojectile stopping screen and target tissue (6–12 cm), for increasing the surface area for maximum particle penetration, minimum cell damage/injury and maximum regeneration efficiency (k) bombardment of leaf explants with biolistic guns like DuPont, Gene booster but specifically Helium powered Particle Delivery system, PDS-1000/He (Bio-Rad) under a chamber pressure of 22 to 28 inches mercury with gold particles (0.6–1.6 µm), together with 1, 2 and 4 µg/µl concentrations of DNA and the above 360 combinations wherein the tissue damage due to gas shock and high particle dispersion was circumvented by increasing the target distance for optimal particle dispersion and simultaneously the tissue damage due to off centred flight of microprojectile flight distance was overcome by decreasing the gap distance (l) bombardment of each plate twice after changing the direction of the Petri-plate by turning it by 180°

(m) turning of the bombarded explants ranging from leaf, somatic embryos, zygotic embryos and embryogenic calli upside down on the regeneration medium with abaxial surface up such that the bombarded surface touches the regeneration medium (n) culturing in dark for two days at a temperature of 25+2° C. of culture lab (o) assay of the bombarded leaves for GUS expression following the method of Jefferson, wherein the reaction of the GUS (5-bromo, 4-chloro, 3-indolyl, β-D-glucuronide) chemical with the transformed leaf explant produced a blue colour 'reaction product' thereby indicating the entry of the pRT99GUS plasmid DNA coated microprojectiles of BioRad into the cells of the explant tissue (Jefferson R A 1987, Assaying chimeric genes in plants: The GUS gene fusion system, Plant Mol Biol Rep 5: 389–405)

(p) transfer of the bombarded leaf explants after two days to the regeneration medium of Sandal I, Bhattacharya A, Sharma M, Ahuja P. S. 'An efficient method for micropropagation of tea (*Camellia sinensis*) plants using leaf explants' patent filed in 2001 under normal photoperiods of 16 h under cool fluorescent light of 52 µmol $m^{-2}s^{-1}$ of the culture lab (q) finally selection of putative transformants after every 15 days on selection medium containing kanamycin (250–1100 µg/ml) (r) regeneration of shoot buds from the completely folded, half opened or fully expanded leaf explants of 3 to 5 months old in vitro raised cultures following the protocol of Sandal I, Bhattacharya A, Sharma M, Ahuja P. S. 'An efficient method for micropropagation of tea (*Camellia sinensis*) plants using leaf explants' patent filed in 2001 (s) growing and multiplying the transgenic shoots in liquid medium of Sandal I, Bhattacharya A, Ahuja P. S. An efficient liquid culture system for tea shoot proliferation Plant Cell Tissue Organ Culture 65(1): 75–80 (2001)(t) molecular characterization of GUS positive tissues of transgenic plants selected on 250–1100 µg/ml kanamycin using PCR and Southern Hybridization following standard methods.

In an embodiment, different explants like leaf, somatic embryos, zygotic embryos and embryogenic calli of different cultivars (*Chinary, Cambod* and *Assamica*) were genetically transformed through biolistics as stated above.

In another embodiment, leaf explants of ex vitro raised plants were treated with liquid basal hormone free MS medium and different osmotic agents wherein the least cumbersome and cheaper MS medium was most effective prior to bombardment with biolistic.

In yet another embodiment, leaf explants were treated with liquid basal hormone free MS medium and different ranges of osmotic agents like sucrose, myoinositol, sorbitol, mannitol alone and in combinations of mannitol and sorbitol wherein full strength hormone free basal MS medium was the most effective.

In still another embodiment, the leaf explants were treated with hormone free liquid basal MS medium and different osmotic agents for different time periods ranging from 2 to 8 hrs wherein hormone free liquid basal MS medium treatment for 4 hours was most effective.

In an embodiment, 50–70 µg gold particle was prepared in sterile water both for direct use and storage in order to overcome the inhibitory effect of remnant glycerol during the loading of DNA onto the macro-carriers.

In yet another embodiment concentric circles of variable diameter ranging from 2.0 to 9.0 cm were drawn on a transparent polythene sheet where the diameter of the outermost circle was same as that of a 9.0 cm petridish.

In an embodiment, explants were arranged with adaxial surface up on the regeneration medium for bombardment.

In another embodiment, the explants were arranged on the regeneration medium within the different concentric circles ranging from 2.0 to 5.0 cm of 9.0 cm Petri-dishes for optimization of the spreading pattern of pRT99GUS plasmid DNA coated micro-projectiles (BioRad) and using GUS assay method of Jefferson (Jefferson R A 1987, Assaying chimeric genes in plants: The GUS gene fusion system, Plant Mol Biol Rep 5: 389–405).

In an embodiment, gold particles ranging from 0.5–1.5 ml were sterilized by washing with 70% alcohol and sterile water for three times each.

In another embodiment, the suspension ranging from 25 to 60 µl was dispensed in 1.5 ml Eppendorf tubes for each bombardment.

In another embodiment, 40–60 µl of gold suspension was mixed with 5–15 µl of different concentrations of pRT99GUS plasmid DNA (0.5–5 µg/µl), 40–60 µl of 1.5–3.5M $CaCl_2$ and 10–50 µl of 0.5–2.0M spermidine free of phosphate salts.

In another embodiment, the suspension was vortexed from time to time, with spinning for 5–20 seconds at 500–1100 rpm followed by removal of the supernatant, washing with 70% ethanol and final suspension in 50–100 µl of 100% ethanol.

In another embodiment, 5–15 µl suspension of gold particles and DNA were coated on sterile macrocarriers (BioRad) with immediate vortexing.

In another embodiment, the explants were bombarded with biolistic guns like DuPont, Gene Booster and Helium powered Particle Delivery system, PDS-1000/He (Bio-Rad) but preferably Helium powered Particle Delivery system, PDS-1000/He (Bio-Rad) under a chamber pressure of 22 to 28 inches mercury.

In another embodiment, 360 combinations were developed comprising of: gap distances or distance between the rupture disc and the macro-carrier (¼–⅜ inches alone and in combination), macrocarrier flight distance or the distance between macrocarrier and stopping screen (6–16 mm), and target distance or distance between the microprojectile stopping screen and target tissue (6–12 cm), for increasing the surface area for maximum particle penetration, minimum cell damage/injury and maximum regeneration efficiency In another embodiment, 360 combinations of the above together with gold particles ranging from 0.6 to 1.6 µm, and concentration ranging from 1, 2 and 4 µg/µl of DNA were used, wherein preferably a combination of 1.0 µm gold particles, 1100 psi burst pressure, target distance (9 cm), gap distance (⅜"+¼" and ¼"), macro-carrier flight distance (16 mm) and 1 µg/µl of DNA gave the maximum transformation frequency.

In another embodiment, each explant was bombarded twice by changing the direction of the Petri-plates by 180°.

In another embodiment, the bombarded explants were turned upside down on the regeneration medium with abaxial surface up.

In another embodiment, the bombarded explants preferably leaf explants were cultured in dark for two days under culture lab conditions of 25+2° C. followed by culture on regeneration medium of Sandal I, Bhattacharya A, Sharma M, Ahuja P. S. 'An efficient method for micropropagation of tea (Camellia sinensis) plants using leaf explants' patent filed in 2001.

In another embodiment, the bombarded explants were tested for transient expression using GUS assay method of Jefferson R A (1987) Assaying chimeric genes in plants: The GUS gene fusion system, Plant Mol Biol Rep 5: 389–405 after 6 days of bombardment.

In another embodiment, the leaf derived calli were selected after every 15 days on selection medium containing kanamycin.

In another embodiment, kanamycin levels ranging from 250–1100 µg/ml kanamycin was used for selection of transformants almost no chance of 'escapes'.

In another embodiment, 1.0 cm long healthy transgenic plants were grown and multiplied on kanamycin free liquid multiplication medium of Sandal I, Bhattacharya A, Ahuja P. S. An efficient liquid culture system for tea shoot proliferation Plant Cell Tissue Organ Culture 65(1): 75–80 (2001).

In another embodiment, GUS positive tissues of transgenic plants selected on 250–1100 µg/ml kanamycin were characterized (molecular) using PCR and Southern Hybridization following standard methods.

In another embodiment of the present invention different explants like somatic embryos and embryogenic calli were used for bombardment with the above parameters.

In still another embodiment of the present invention leaf explants of different cultivars were used for bombardment from both in vitro and ex vitro plants.

(i) Leaf explants were treated with liquid basal hormone free MS medium (Murashige T. and Skoog F. A revised medium for rapid growth and bioassays with tobacco tissue cultures. Physiol. Plant. 15: 473–497; 1962) and different concentrations of osmotic agents like sucrose, myoinositol, sorbitol, mannitol alone and combinations of mannitol and sorbitol for different time periods (2–8 hrs).

(ii) Concentric circles were drawn on a transparent polythene sheet wherein the diameter of the outermost circle was same as that of a 9.0 cm petridish.

(iii) Arrangement of leaf explants with adaxial surface up on the regeneration medium within the different concentric circles (2.0–5.0 cm ) of 9.0 cm Petri-dishes for maximum spread of DNA coated micro-projectiles.

(iv) Gold particles of 0.5–1.5 ml were suspended in sterile distilled water after washing with 70% alcohol and sterile water for three times each.

(v) The suspension (25–60 µl ) was dispensed in 1.5 ml Eppendorf tubes for each bombardment.

(vi) 50 µl of gold suspension was mixed with 10 µl of different concentrations of plasmid DNA (0.5–5 µg/µl), 40–50 µl of 1.5–3.5M $CaCl_2$ and 10–50 µl of 0.5–2.0M spermidine free phosphate salts.

(vii) The suspension was vortexed from time to time, with spinning for 5–20 seconds at 500–1100 rpm followed by removal of the supernatant and washing with 70% ethanol and final suspension in 50–100 μl of 100% ethanol.

(viii) 10 μl suspension of gold particles and DNA were coated on sterile macrocarriers (BioRad) with immediate vortexing.

(ix) The 354 combinations were developed that comprised of: (a) gap distances or distance between the rupture disc and the macro-carrier (¼–⅜ inches alone and in combination), (b) macrocarrier flight distance or the distance between macrocarrier and stopping screen (6–16 mm), (c) target distance or distance between the microprojectile stopping screen and target tissue (6–12 cm), and burst pressure (650–1350 psi) of the rupture discs (BioRad) for increasing the surface area for maximum particle penetration, minimum cell damage/injury and maximum regeneration efficiency.

(x) The leaf explants were bombarded with Helium powered Particle Delivery system, PDS-1000/He (Bio-Rad) under a chamber pressure of 25 inches Hg with 0.6–1.6 μm gold particles, 1, 2 and 4 μg/μl concentrations of DNA and the 354 combinations that were derived above.

(xi) Each plate was twice bombarded by changing the direction of the Petri-plate by 180° C.

(xii) The bombarded explants were turned upside down on the regeneration medium with the abaxial surface up such that the bombarded surface touches the regeneration medium for rapid healing.

(xiii) The bombarded leaf explants were cultured in dark for two days under culture lab conditions.

(xiv) The bombarded leaf explants were tested for transient expression using GUS assay method of Jefferson R A (1987) Assaying chimeric genes in plants: The GUS gene fusion system, Plant Mol Biol Rep 5: 389–405 in order to test the maximum spread of particle penetration.

(xv) After two days, the bombarded leaf explants were transferred to the regeneration medium of Sandal I, Bhattacharya A, Sharma M, Ahuja P. S. 'An efficient method for micropropagation of tea (Camellia sinensis) plants using leaf explants' patent filed in 2001 under normal photoperiod of culture lab conditions (xvi) Shoot buds were regenerated from bombarded leaf explants following the protocol of Sandal I, Bhattacharya A, Sharma M, Ahuja P. S. 'An efficient method for micropropagation of tea (Camellia sinensis) plants using leaf explants' patent filed in 2001.

(xvii) The putative transformants were selected after every 15 days on selection medium containing kanamycin (250–1100 μg/ml).

(xviii) The putative transgenic shoots were grown and multiplied in liquid medium of Sandal I, Bhattacharya A, Ahuja P. S. An efficient liquid culture system for tea shoot proliferation Plant Cell Tissue Organ Culture 65(1): 75–80 (2001)Sandal I, Bhattacharya A, Ahuja P. S. 2001.

(xix) The GUS positive tissues of transgenic plants selected on 250–1100 μg/ml kanamycin were characterized using PCR and Southern Hybridization following standard methods.

Optimization of parameters for maximum transient expression in tea leaf explants is shown in Table 1.

For successful production of transgenics through biolistic it was felt necessary to optimally combine all the different parameters that affect biolistics in order to (a) increase the surface area for maximum particle penetration (b) minimize cell damage/injury and (iii) maximize regeneration efficiency.

Use of one or two parameters depending upon the texture (hard or soft) of the tissue and the source material (genus or species) for the production of transgenics have been reported in several crops. However, the novelty of this invention is the development of a checker board of all the parameters that affect the success of biolistics that can be universally employed. With the help of these 354 combinations of the checker board (comprising of the combinations of burst pressure of rupture disc, macrocarrier flight distance, target distance and gap distance), any transformation experiment can be successful irrespective of genus, crop or tissue. Pretreatment with osmoticum and concentration of DNA can further improve the transformation efficiency.

Pretreatment with liquid basal hormone free MS (Murashige T. and Skoog F. A revised medium for rapid growth and bioassays with tobacco tissue cultures. Physiol. Plant. 15: 473–497; 1962) medium or 0.25M sorbitol for 4 hrs not only resulted in leathery texture of the tea leaf explants thereby enabling them to be flattened on the regeneration medium and providing a larger surface area for bombardment with minimum injury but also for healing the injury that was caused due to particle penetration. Generally, treatment with an osmotic agent prior to bombardment enhances transient expression considerably as it brings about plasmolysis of the target cells. Plasmolysis prevents the extrusion of protoplasm from cells and further reduces cell damage following particle penetration during bombardment Vain P, McMullen M. D., Finer J. J, 1993 Osmotic treatment enhances particle bombardment mediated transient and stable transformation of maize. Plant Cell Rep 12, 84–88. Tissue pretreatment induces DNA replication resulting in a higher level of insertion of DNA into the genome (.

Path traversed by the gold particles from the stopping screen to the target tissue is generally conical in form. Therefore, overlapping of the surface area of the base of this cone with the defined concentric circles on the regeneration medium on which the explants to be bombarded are arranged for maximum that dispersion of gold particle is required. Therefore a method was devised to draw concentric circles of variable diameters (2.0–9.0 cm) on a transparent polythene sheet wherein the diameter of the outermost circle was same as that of a 9.0 cm petridish. By placing the petridish containing the target tissue on these circles and assaying them for transient expression through GUS after bombardment revealed that a concentric circle with a diameter of 2.0 cm was optimal. This is the reason why maximum particle penetration was achieved when the tea leaf explants were arranged within this area.

An increase in the burst pressure of the rupture disc, the microprojectile velocity increases tissue damage due to gas shock and high particle dispersion and results in low transient gene expression. This was circumvented by either increasing the target distance or by keeping the tissue at a longer distance from the stopping screen for particle dispersion.

BRIEF DESCRIPTION OF THE
ACCOMPANYING DRAWINGS

The patent or application file contains at least one drawing executed in color. Copies of this patent or patent application publication with color drawing(s) will be provided by the Office upon request and payment of the necessary fee.

In the drawing(s) accompanying this specification

FIG. 1a.b.c. represents: Leaf explant of tea plants

FIG. 1d to r represents: different transformed leaf explant showing gus expression The following examples have been provided by way of illustration and should not be construed as limitations on the inventive concept herein.

EXAMPLE-1

Leaf explants of in vitro raised plants were treated with basal MS (Murashige T. and Skoog F. A revised medium for rapid growth and bioassays with tobacco tissue cultures. Physiol. Plant. 15: 473–497; 1962) medium and different concentrations of osmotic agents like sucrose, myoinositol, sorbitol, mannitol alone and different combinations of mannitol and sorbitol for different time periods (2–8 hrs). The treated leaf explants were arranged with adaxial surface up on the regeneration medium within the different concentric circles (2.0–5.0 cm) of 9.0 cm Petri-dishes for optimization of the spreading pattern of DNA coated micro-projectiles. For bombardment gold particles in 0.5–1.5 ml were suspended in sterile distilled water after washing with 70% alcohol and sterile water for three times each and the suspension (25–60 μl) was dispensed in 1.5 ml Eppendorf tubes. For preparation of DNA mix with 50 μl of gold suspension, 10 μl of different concentrations of plasmid DNA (0.5–5 μg/μl), 40–50 μl of 1.5–3.5M $CaCl_2$ and 10–50 μl of 0.5–2.0M spermidine free base. The suspension was vortexed from time to time, with spinning for 5–20 seconds at 500–1100 rpm followed by removal of the supernatant and washing with 70% ethanol and final suspension in 50–100 μl of 100% ethanol. 10 μl suspension of gold particles and DNA were coated on sterile macrocarriers with immediate vortexing. The leaf explants were then bombarded with Helium powered Particle Delivery system, PDS-1000/He (Bio-Rad) under a chamber pressure of 25 inches Hg at 354 combinations together with 0.6–1.6 μm gold particles, 1, 2 and 4 μg/μl concentrations of DNA and each plate was twice bombarded by changing the direction of the Petri-plates. The bombarded explants were turned upside down on the regeneration medium with abaxial surface up. The bombarded leaf explants were cultured in dark for two days under culture lab conditions followed by culture on regeneration medium of Sandal I, Bhattacharya A, Sharma M, Ahuja P. S. 'An efficient method for micropropagation of tea (*Camellia sinensis*) plants using leaf explants' patent filed in 2001 after assaying for GUS expression following the method Jefferson R A (1987) Assaying chimeric genes in plants: The GUS gene fusion system, Plant Mol Biol Rep 5: 389–405. Finally the leaf derived calli were selected after every 15 days on selection medium containing 250–1100 μg/ml kanamycin. The GUS positive tissues of transgenic plants selected on 250–1100 μg/ml kanamycin were characterized (molecular) using PCR and Southern Hybridization following standard methods.

EXAMPLE-2

Leaf explants of ex vitro raised plants were treated with different concentrations of osmotic agents and then transformed genetically through biolistics as stated above.

EXAMPLE-3

Leaf explants of plants of different cultivars (*Chinary, Cambod* and *Assamica*) were treated with different concentrations of osmotic agents and then transformed genetically through biolistics as stated above.

EXAMPLE-4

Different explants like somatic embryos, zygotic embryos and embryogenic calli were transformed genetically through biolistics as stated above.

The novelty of the method is that a checker board comprising of 354 combinations was developed which ensures the success of biolistic mediated transgenic production irrespective of the type of tissue, explant or genus.

Some of the novel features that were introduced are as follows:

1. Basal hormone free MS (Murashige T. and Skoog F. A revised medium for rapid growth and bioassays with tobacco tissue cultures. Physiol. Plant. 15: 473–497; 1962) medium has been used for the first time instead of an osmoticum and this prevents the cumbersome and costly pretreatment steps with known osmotic agents.
2. Concentric circles of variable diameter (2.0–9.0 cm) were drawn on a transparent polythene sheet wherein the diameter of the outermost circle was same as that of a 9.0 cm petridish so that the exact area where the target tissue had to be placed would be known prior to bombardment. Moreover, this would also enable the maximization of the area for particle penetration.
3. Gold particles were suspended in water instead of glycerol for the first time in order to overcome the problems of inhibitory effects of remnant glycerol during loading of the DNA onto the macrocarriers.
4. A step for faster healing of the injuries due to particle penetration was devised by turning the leaves upside down after bombardment. This enabled the injured sites to come in contact with the medium and also resulted in faster regeneration response.
5. The responsive leaf explants i. e. after formation of the leaf callus were selected on a very high dose of kanamycin i.e. 500 or 1000 μg/ml in order to prevent any 'escapes' and ensure a high percentage of stable transformants (95–100%). This is the first report of using kanamycin at a dose as high as 1000 μg/ml for selection of transformants.
6. This method also ensures production of healthy transformed tea shoots.

The main advantages of the present invention are

1) Elite plants to be made resistant to fungal diseases like blister blight by production of transgenics through biolistic inorder to overcome the 50% crop loss.
2) Elite plants to be made resistant to bacterial diseases like bacterial shoot blight by production of transgenics through biolistic.
3) Elite plants to be made resistant to viral diseases by production of transgenic through biolistic.
4) Elite plants to be made resistant to tea resistant to pests like insects, thrips and mites by production of transgenics through biolistic.
5) Elite plants to be made resistant to herbicides like glyphosate, 2,4-D, paraquat and Diuron and pre-emergence herbicides like atrazine and oxyflurfon by production of transgenic through biolistic.
6) Elite plants to be made resistant to different stresses by (i) overexpressing genes encoding enzymes for increased oxygen radical scavenging (ii) for increased contents of osmolytes like mannitol, proline, fructans, gycine-betaine etc. (Bonhert et al., 1996; Hayashi et al., 1997), (iii) improving the flexibility of cell membranes and (iv) engineering the expression of stress-induced proteins like LEA proeins, dehydrins, antifreeze proteins (AFPs), heat shock proteins (HSPs) and hypoxia and anoxia reducing proteins like the VHb proteins by production of transgenics through biolistics.
7) Production of transgenic tea resistant to weeds like grasses, broad leaf weeds etc.
8) Production of transgenic tea with little or no winter dormancy.
9) Production of transgenic plants expressing genes like APETALA or LEAFY under specific promoter control for increased number of vegetative shoots.
10) Production of transgenic tea genes encoding RUBPcase under suitable promoters for enhanced photosynthetic rates.
11) Production of transgenic tea over expressing phytochrome gene for dense planting and good tea tables for easier plucking.
11) Production of tea plants with higher yield and good cup quality.
12) Improvement of elite plants for improved quality and yield by production of transgenics through biolistic.
13) Production of de-caffeinated transgenic tea plants.
14) Production of transgenic tea plants with sweet tea leaves using genes like thaumatin and lectins etc.
15) To provide a biolistic mediated genetic transformation method for high rates of transgenic production irrespective of genus, crop, tissue, explant etc.
16) To overcome certain problems that are faced during some steps of biolistic mediated genetic transformation.

TABLE 1

Optimization of parameters for maximum transient expression in tea leaf explants

| Pressure | TD 3 cm | 6 cm | 9 cm | 12 cm | MFD |
|---|---|---|---|---|---|
| 650 psi | 900, 3 cm, 6 mm*, | 900, 6 cm, 6 mm* | 900, 9 cm, 6 mm* | 900, 12 cm, 6 mm* | 6 mm |
|  | 900, 3 cm, 11 mm* | 900, 6 cm, 11 mm* | 900, 9 cm, 11 mm* | 900, 12 cm, 11 mm* | 11 mm |
|  | 900, 3 cm, 16 mm* | 900, 6 cm, 16 mm* | 900, 9 cm, 16 mm* | 900, 12 cm, 16 mm* | 16 mm |
| 900 psi | 900, 3 cm, 6 mm, | 900, 6 cm, 6 mm* | 900, 9 cm, 6 mm* | 900, 12 cm, 6 mm* | 6 mm |
|  | 900, 3 cm, 11 mm* | 900, 6 cm, 11 mm* | 900, 9 cm, 11 mm* | 900, 12 cm, 11 mm* | 11 mm |
|  | 900, 3 cm, 16 mm* | 900, 6 cm, 16 mm* | 900, 9 cm, 16 mm* | 900, 12 cm, 16 mm* | 16 mm |
| 1100 psi | 1100, 3 cm, 6 mm* | 1100, 6 cm, 6 mm* | 1100, 9 cm, 6 mm* | 1100, 12 cm, 6 mm* | 6 mm |
|  | 1100, 3 cm, 11 mm* | 1100, 6 cm, 11 mm* | 1100, 9 cm, 11 mm* | 1100, 12 cm, 11 mm* | 11 mm |
|  | 1100, 3 cm, 16 mm* | 1100, 6 cm, 16 mm* | 1100, 9 cm, 16 mm* | 1100, 12 cm, 16 mm* | 16 mm |
| 1350 psi | 1350, 3 cm, 6 mm* | 1350, 6 cm, 6 mm* | 1350, 9 cm, 6 mm* | 1350, 12 cm, 6 mm* | 6 mm |
|  | 1350, 3 cm, 11 mm* | 1350, 6 cm, 11 mm* | 1350, 9 cm, 11 mm* | 1350, 12 cm, 11 mm* | 11 mm |
|  | 1350, 3 cm, 16 mm* | 1350, 6 cm, 16 mm* | 1350, 9 cm, 16 mm* | 1350, 12 cm, 16 mm* | 16 mm |
| 1550 psi | 1550, 3 cm, 6 mm* | 1550, 6 cm, 6 mm* | 1550, 9 cm, 6 mm* | 1550, 12 cm, 6 mm* | 6 mm |
|  | 1550, 3 cm, 11 mm* | 1550, 6 cm, 11 mm* | 1550, 9 cm, 11 mm* | 1550, 12 cm, 11 mm* | 11 mm |
|  | 1550, 3 cm, 16 mm* | 1550, 6 cm, 16 mm* | 1550, 9 cm, 16 mm* | 1550, 12 cm, 16 mm* | 16 mm |

Six GAP distances (3/8", 1/4", 1/8", 3/8" + 1/4", 3/8" + 1/8", 3/8" + 1/8" + 1/4") were tested for each of the above 27 combinations.

The invention claimed is:

1. A method for producing a transgenic tea plant, comprising (a) maintaining a tea explant in a medium that comprises at least one osmotic agent; (b) bombarding the explant with glycerol-free metal particles that are coated with a desired DNA and then placing the bombarded surface of the explant in direct contact with the medium; (c) determining the presence of the desired DNA in one or more cells of the explant; and (d) culturing an explant that comprises the desired DNA in one of its cells into a plant, wherein the bombardment path of the metal particles and the position of the explant are aligned for maximum particle penetration, and wherein the plant that comprises the desired DNA in one of its cells is a transgenic tea plant.

2. The method of claim 1, wherein the tea explant is an explant from *Camellia sinensis*.

3. The method of claim 1, wherein the osmotic agent is at least one of sucrose, myoinositol, sorbitol, and mannitol.

4. The method of claim 1, wherein the concentration of the osmotic agent is about 0.25–0.75 M.

5. The method of claim 1, wherein the medium further comprises a vitamin that is thiamine-HCl, pyridoxine-HCl, or nicotinic acid.

6. The method of claim 1, wherein the tea explant is maintained on the medium from 2 to 8 hours.

7. The method of claim 1, wherein the medium is Murashige and Skoog medium.

8. The method of claim 1, wherein the step of bombarding the explant with glycerol-free metal particles is conducted in a chamber that is appropriate for particle bombardment.

9. The method of claim 8, wherein the chamber is part of a biolistic transformation device.

10. The method of claim 9, wherein the device is a gas powered particle delivery system.

11. The method of claim 10, wherein the gas is helium.

12. The method of claim 11, wherein the device is the PDS-1000/He particle delivery system.

13. The method of claim 8, wherein the step of bombarding the explant with glycerol-free metal particles is conducted when the chamber is under a vacuum.

14. The method of claim 13, wherein the pressure of the vacuum in the chamber is from about 22 to about 28 inches of mercury.

15. The method of claim 1, wherein the metal particles are gold particles.

16. The method of claim 15, wherein the diameter of each of the gold particles is from about 0.6 to about 1.6 μm.

17. The method of claim 1, wherein the metal particles are suspended in a glycerol-free solution that comprises about 0.5 to about 5 μg/μl of the desired DNA.

18. The method of claim 17, wherein the solution further comprises calcium chloride and spermidine.

19. The method of claim 18, wherein the concentration of the calcium chloride is from about 1.5 to about 5.3 M.

20. The method of claim 18, wherein the concentration of the spermidine is from about 0.5 to about 2.0 M.

21. The method of claim 1, wherein the explant is a leaf, somatic embryo, zygotic embryo, or a callus.

22. The method of claim 1, wherein multiple explants are positioned in concentric circles and aligned so as to be in the path of the bombardment particles, thereby enhancing or achieving maximum particle penetration.

23. The method of claim 22, wherein the explants are in a particle delivery system comprising (i) a gas-driven acceleration tube, (ii) a rupture disc, (iii) a macrocarrier, which holds the DNA-coated particles, and (iv) a stopping screen.

24. The method of claim 23, wherein any one of the distances between (i) the rupture disc and the macrocarrier, (ii) the macrocarrier and the stopping screen, and (iii) the stopping screen and the explant, can be adjusted.

25. The method of claim 24, wherein (i) the distance between the rupture disc and the macrocarrier is not more than about 1.3 cm, (ii) the distance between the macrocarrier and the stopping screen is about 1.6 cm, and (iii) the distance between the stopping screen and the explant is about 9 cm.

26. The method of claim 23, wherein the burst pressure of the gas released from the acceleration tube is about 1100 psi.

27. The method of claim 23, wherein the concentration of DNA coated onto the particles is about 1 µg/µl.

28. The method of claim 1, wherein, after the explants have been bombarded once and before the step of determining the presence of the desired DNA in one or more cells of the explant, the position of the explants is rotated by 180 degrees and then the explants are bombarded again.

29. The method of claim 1, wherein the step of culturing an explant that comprises the desired DNA in one of its cells into a plant, comprises (i) placing the bombarded surface of the explant in contact with the medium, (ii) leaving the explants in the dark for two days at a temperature of about 23° C. to about 27° C., (iii) transferring the explant to regeneration medium, and (iv) selecting a transformed explant that has been successfully transformed with the desired DNA to grow into a transgenic tea plant.

\* \* \* \* \*

UNITED STATES PATENT AND TRADEMARK OFFICE
CERTIFICATE OF CORRECTION

PATENT NO.         : 7,129,394 B2                                           Page 1 of 1
APPLICATION NO.    : 10/051383
DATED              : October 31, 2006
INVENTOR(S)        : Indra Sandal, Amita Bhattacharya and Paramvir Singh Ahuja It is certified that error appears in the above-identified patent and that said Letters Patent is hereby corrected as shown below:

Item (73) Assignee Please insert Council of Scientific and Industrial Research, New Delhi (IN)

Signed and Sealed this

Sixth Day of March, 2007

JON W. DUDAS
*Director of the United States Patent and Trademark Office*